United States Patent [19]

Fuchs et al.

[11] Patent Number: 4,683,305

[45] Date of Patent: Jul. 28, 1987

[54] OBTAINING CAPROLACTAM BY CLEAVING OLIGOMERS OF CAPROLACTAM

[75] Inventors: Hugo Fuchs, Ludwigshafen; Uwe Brand, Lampertheim; Helmut Buchaeckert, Boehl-Iggelheim, all of Fed. Rep. of Germany

[73] Assignee: BASF Aktiengesellschaft, Ludwigshafen, Fed. Rep. of Germany

[21] Appl. No.: 883,177

[22] Filed: Jul. 8, 1986

[51] Int. Cl.[4] ............................................. C07D 201/12
[52] U.S. Cl. .................................... 540/533; 540/540
[58] Field of Search ................................ 540/540, 533

[56] References Cited

FOREIGN PATENT DOCUMENTS 0046183 2/1982 European Pat. Off. ............ 540/540

Primary Examiner—Robert T. Bond
Attorney, Agent, or Firm—Keil & Weinkauf

[57] ABSTRACT

Caprolactam is obtained by cleaving oligomers of caprolactam by a process in which the oligomers, in a liquid or solid state, are introduced into a fluidized alumina bed and cleaved at from 290° to 400° C. in the presence of steam, and, in addition to the amount of inert gas required to fluidize the alumina bed, from 0.1 to 3 times this amount of inert gas is introduced above the fluidized bed.

4 Claims, No Drawings

OBTAINING CAPROLACTAM BY CLEAVING OLIGOMERS OF CAPROLACTAM

German Laid-Open Application DOS No. 3,030,735 discloses a process for obtaining caprolactam by cleaving oligomers of caprolactam, in which the oligomers, in a liquid or solid state, are introduced into a fluidized alumina bed and cleaved at from 290° to 400° C. in the presence of steam. However, it has been found that this procedure leads to blockage of the vapor lines, making it necessary to interrupt operation frequently.

It is an object of the present invention to provide a process for the cleavage of oligomers of caprolactam in a fluidized alumina bed, in which blockage of the vapor lines, and associated frequent interruptions, do not occur.

We have found that this object is achieved by a process for obtaining caprolactam by cleaving oligomers of caprolactam, in which the oligomers, in a liquid or solid state, are introduced into a fluidized alumina bed and cleaved at from 290° to 400° C. in the presence of steam, wherein, in addition to the amount of inert gas required to fluidize the alumina bed, from 0.1 to 3 times this amount of inert gas is introduced above the fluidized bed.

The novel process has the advantages that virtually no blockage occurs and the process can be carried out over a long period without interruption, and abrasion in the fluidized alumina bed is substantially reduced.

Oligomers which are used as starting materials have, as a rule, a degree of polymerization n of from 2 to 9 and contain, in particular, dimeric and trimeric cyclic oligomers. Such oligomers are obtained, for example, by evaporating down wash waters produced in the extraction of polycaprolactam and then removing the monomeric caprolactam by distillation. Advantageously, the oligomers are used as a mixture with caprolactam. It is therefore not necessary to distill off the total amount of caprolactam from the extract obtained. Suitable mixtures contain, for example, from 10 to 60% by weight of oligomers and from 90 to 40% by weight of caprolactam. The oligomers or the mixtures of oligomers and caprolactam are advantageously introduced in liquid form, ie. in the molten state, for example at from 150° to 250° C., into a fluidized alumina bed. However, it is also possible to introduce the oligomers or the oligomer/lactam mixture in solid, finely divided form into the fluidized bed, and to cleave the oligomers catalytically to give monomeric caprolactam. Introduction into the fluidized bed is effected, for example, by blowing in by means of a nozzle operated with the inert gas.

Suitable aluminum oxides are the various modifications, such as alumina or boehmite, and γ-alumina has proven a very useful catalyst. The catalyst is kept in a fluidized state with an inert gas, such as carbon dioxide, argon or nitrogen, preferably nitrogen. Alumina having particle sizes of from 0.05 to 1.5, in particular from 0.2 to 1, mm is advantageously used. The height of the catalyst bed is preferably chosen so that the residence times of the oligomers over the catalyst bed are from 0.1 to 30, in particular from 0.5 to 10, seconds. The process is advantageously carried out under atmospheric pressure, although slightly reduced or slightly superatmospheric pressure, eg. up to 2 bar, may also be employed.

The catalyst bed is kept at from 290° to 400° C., in particular from 300° to 360° C. Hence, it is also advantageous to feed the inert gas at from 290° to 400° C. into the fluidized bed.

An essential feature of the invention is that inert gas is not introduced just into the fluidized bed, in order to fluidize alumina or to introduce the oligomers to be cleaved, but a further amount of inert gas is additionally fed in above the fluidized bed. According to the invention, in addition to the amount of inert gas required to fluidize the alumina bed, from 0.1 to 3 times this amount of inert gas is therefore fed in above the fluidized bed. It has furthermore proven advantageous to maintain in the fluidized bed a fluidization velocity of from 10 to 40 m/sec, based on the free cross-section.

A caprolactam partial pressure of from 50 to 300 mbar is advantageously maintained in the gas space above the fluidized bed.

Cleavage is carried out in the presence of steam, from 0.005 to 10, in particular from 0.02 to 2, parts by weight of water in the form of steam advantageously being used per part by weight of oligomers. The water to be used may be introduced into the fluidized bed as such and vaporized there, but is preferably added in the form of steam. For example, the steam may be introduced into the fluidized bed together with the inert gas.

The gas mixture emerging from the fluidized bed is condensed in a bubble tray column by adding water at the top of the column, as described in, for example, German Published Application DAS No. 1,445,549. Caprolactam is obtained as the bottom product, while the inert gas and steam escape at the top of the column. The steam can be condensed from the inert gas, which is advantageously recycled into the fluidized bed and to the space above this bed.

The condensed caprolactam can be purified again, for example by distillation, and the caprolactam recovered in this manner can then be added to the caprolactam obtained from the Beckmann rearrangement and requiring purification, and the mixture can be purified, as described in, for example, German Pat. No. 1,194,863.

It is also possible to condense the caprolactam out of the vapor mixture emerging from the reactor, as described, and to add this directly to the crude lactam from the Beckmann rearrangement, and to work up these products jointly.

Caprolactam is used for the production of polycaprolactam. The Examples which follow illustrate the process according to the invention.

COMPARATIVE EXAMPLE

A fluidized bed consisting of 1200 kg of alumina is maintained in a vertical reactor which has a diameter of 1000 mm and in which the gas space above the fluidized bed has a diameter of 1500 mm. The mean particle size of the alumina is from 200 to 500 μm. The catalyst is fluidized by blowing in a stream of 300 kg/hour of preheated nitrogen from below through a perforated base. 60 kg/hour of steam are fed into the nitrogen. The fluidized bed is maintained at from 290° to 300° C.

400 kg/hour of a mixture of caprolactam and oligomers, having an oligomer content of 12% by weight, are introduced by spraying, with 30 kg/hour of nitrogen per nozzle, through two nozzles which are located 180° apart along the circumference of the reactor and about 500 mm above the perforated base. The fluidization velocity is 29.6 cm/sec, based on the free cross-section, the caprolactam partial pressure is 199.7 mbar and the residence time is 6.4 sec.

The vapor mixture leaving the reactor flows through a cyclone to separate off the catalyst dust and then passes into a column, in which the caprolactam is condensed by adding water at the top of the column. In this way, 396.3 kg/hour of caprolactam having a residual oligomer content of about 0.1% by weight are obtained. In this procedure, 23 kg/day of catalyst dust are produced. After an operating period of 6 weeks, the amount of deposits in the vapor lines made it necessary to remove these deposits mechanically. The caprolactam partial pressure in the vapor line was 199.7 mbar.

EXAMPLE

As described in the Comparative Example, 400 kg of a mixture of caprolactam and oligomers, having an oligomer content of 12% by weight, are introduced through the nozzles into the fluidized bed, at the same height as in the Comparative Example, using 30 kg/hour of nitrogen per nozzle. However, the amount of nitrogen used to fluidize the catalyst is only 160 kg/hour. The amount of steam introduced into the reactor together with the nitrogen stream is 60 kg/hour. The fluidized bed is maintained at from 290° to 300° C. 200 kg/hour of nitrogen are additionally introduced into the gas space of the reactor, above the fluidized bed.

The fluidization velocity is 22.1 cm/sec, based on the free cross-section, the caprolactam partial pressure is 267.5 mbar and the residence time is 8.6 sec. 396.6 kg/hour of caprolactam having a residual oligomer content of about 0.1% by weight are obtained from the vapors.

In this procedure, no deposits are found in the vapor lines, even after 16 weeks. The caprolactam partial pressure in the vapor line is 180.1 mbar.

We claim:

1. A process for obtaining caprolactam by cleaving oligomers of caprolactam, wherein the oligomers, in a liquid or solid state, are introduced into a fluidized alumina bed and cleaved at from 290° to 400° C. in the presence of steam, and, in addition to the amount of inert gas required to fluidize the alumina bed, from 0.1 to 3 times this amount of inert gas is introduced above the fluidized bed.

2. The process of claim 1, wherein a fluidization velocity of from 10 to 40 cm/sec, based on the free cross-section, is maintained in the fluidized bed.

3. The process of claim 1, wherein a caprolactam partial pressure of from 50 to 300 mbar is maintained in the gas space above the fluidized bed.

4. The process of claim 1, wherein the inert gas introduced above the fluidized bed is nitrogen.

* * * * *